(12) United States Patent
Menard et al.

(10) Patent No.: US 6,264,784 B1
(45) Date of Patent: Jul. 24, 2001

(54) ABSORBENT ARTICLE WITH ATTACHED TABS AND METHOD AND APPARATUS FOR MAKING SAME

(75) Inventors: Michael Joseph Menard, Doylestown, PA (US); Paul Fung, South River, NJ (US)

(73) Assignee: Johnson & Johnson Inc., Montreal (CA)

( * ) Notice: Subject to any disclaimer, the term of this patent is extended or adjusted under 35 U.S.C. 154(b) by 0 days.

(21) Appl. No.: 08/344,963

(22) Filed: Nov. 25, 1994

Related U.S. Application Data

(63) Continuation of application No. 08/195,893, filed on Feb. 10, 1994, now abandoned, which is a continuation of application No. 07/766,982, filed on Sep. 27, 1991, now abandoned.

(51) Int. Cl.[7] ..................................................... B32B 31/00
(52) U.S. Cl. ........................................... 156/250; 156/164
(58) Field of Search ..................................... 156/250, 164, 156/567, 571, 575; 604/390, 395, 387, 385.1, 385.2

(56) References Cited

U.S. PATENT DOCUMENTS

| | | | |
|---|---|---|---|
| 2,890,701 | * | 6/1959 | Weinman ............................. 604/398 |
| 3,728,191 | * | 4/1973 | Wierzba . | |
| 3,878,283 | | 4/1975 | Jones .................................... 264/152 |
| 3,897,293 | * | 7/1975 | Babcock . | |
| 3,924,626 | * | 12/1975 | Lee et al. .......................... 604/385.1 |
| 4,285,343 | * | 8/1981 | McNair ................................. 128/287 |
| 4,332,635 | * | 6/1982 | Holbrook et al. .................... 156/567 |
| 4,589,876 | * | 5/1986 | Van Tilburg .......................... 604/393 |
| 4,608,047 | * | 8/1986 | Mattingly .............................. 604/387 |
| 4,666,542 | * | 5/1987 | De Jonckheere ..................... 156/164 |
| 4,678,527 | * | 7/1987 | Ulman ................................... 156/213 |
| 4,701,178 | * | 10/1987 | Glaug et al. .......................... 604/287 |
| 4,726,876 | * | 2/1988 | Tousovic, Jr. ......................... 156/567 |

(List continued on next page.)

FOREIGN PATENT DOCUMENTS

| | | | |
|---|---|---|---|
| 280998 | 9/1988 | (EP) | ............................... A61F/13/18 |
| 2644694 | 9/1990 | (FR) | ............................... A61F/13/46 |
| 1217402 | 12/1967 | (GB) | ............................... A61F/13/15 |
| 2048684 | * 12/1980 | (GB) | ............................... A61F/13/16 |

*Primary Examiner*—Merrick Dixon

(57) ABSTRACT

A method and apparatus is provided for forming and attaching tabs to an absorbent article worn in the perineal portion of the body, such as sanitary napkins. A strip of tab material is cut into two tab strips by making an approximately sinusoidal shaped longitudinal cut using a rotary die. The tab strips are then inverted so the tabs face outward and aligned so that the tabs are in-line. The tab strips are then cut into tab pairs and attached to a strip of absorbent article using an adhesive. In an alternate embodiment, the tab pairs are first attached to a layer of material which is then attached to a second layer of material on which an absorbent core is disposed, thereby enclosing the absorbent core. An absorbent article made by the aforementioned method and apparatus is also provided. The article has a central portion and tabs attached to the portions of the longitudinally extending sides of the central portion which are adjacent the body facing said of the article, thereby preferentially creating tension in the pervious cover forming the body facing side and inducing compressive forces acting on the absorbent core which aid it in resisting lateral deformation. The central portion has an article release strip covering pressure sensitive adhesive strips on its garment facing side and the tabs have tab release strips covering pressure sensitive adhesive strips on their garment facing sides. The tabs are disposed over the garment facing side of the central portion and adhesive is applied between the article release strip and tab release strips, attaching each to the other so that both the article release strip and the tab release strips can be removed by a single pull on the article release strip.

12 Claims, 9 Drawing Sheets

U.S. PATENT DOCUMENTS

| | | | |
|---|---|---|---|
| 4,759,754 | * | 7/1988 | Korpman . |
| 4,760,764 | | 8/1988 | De Jonckheere et al. ............... 83/23 |
| 4,816,105 | * | 3/1989 | Yamashita ............................ 156/567 |
| 4,862,574 | * | 9/1989 | Seidy . |
| 4,900,320 | * | 2/1990 | McCoy . |
| 4,911,701 | * | 3/1990 | Mavinkurve ...................... 604/385.2 |
| 4,917,697 | * | 4/1990 | Osborn, III et al. ................ 604/387 |
| 4,940,462 | * | 7/1990 | Salerno ................ 604/387 |
| 4,950,264 | * | 8/1990 | Osborn, III ........................ 604/385 |

* cited by examiner

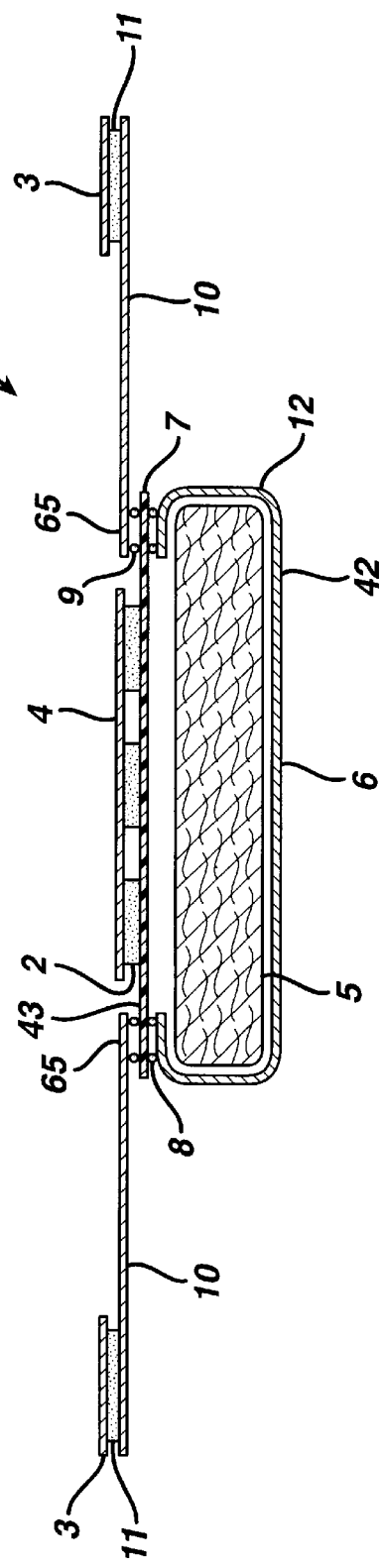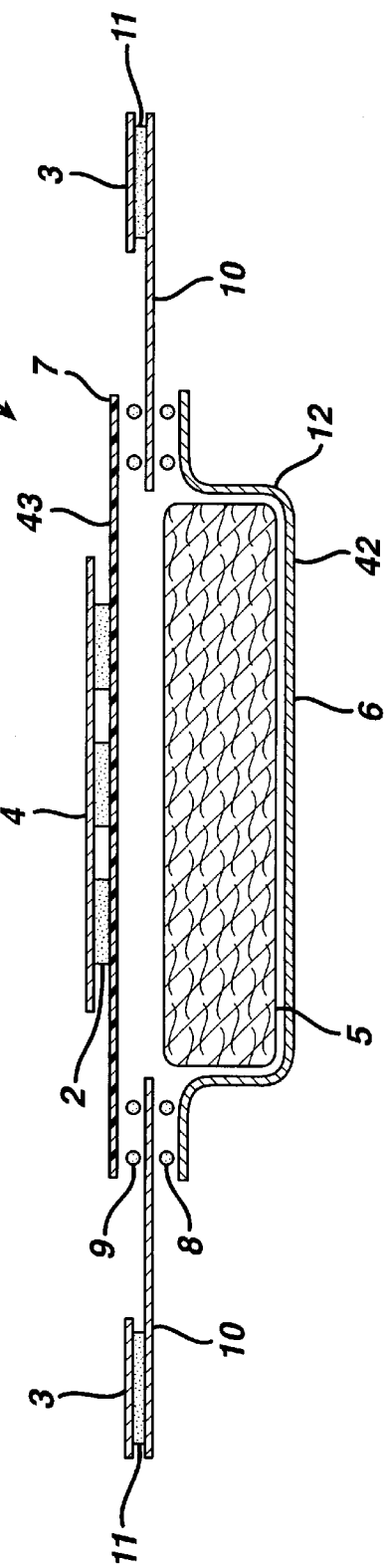

ABSORBENT ARTICLE WITH ATTACHED TABS AND METHOD AND APPARATUS FOR MAKING SAME

This is a continuation of application Ser. No. 08/195,893, filed Feb. 10, 1994, now abandoned; which is a continuation of Ser. No. 07/766,982 filed Sep. 27, 1991, now abandoned.

FIELD OF THE INVENTION

The current invention concerns a method and apparatus for making absorbent articles. More specifically, the invention concerns a method and apparatus for forming and attaching tabs onto an absorbent article designed to be worn in the perineal area of the body, such as sanitary napkins, incontinence pads and the like. The current invention also concerns an absorbent article made by the apparatus and method.

BACKGROUND OF THE INVENTION

Traditionally, absorbent articles have included a central absorbent element having a body facing side, a garment facing side, longitudinally extending sides and transverse ends. These articles generally include an absorbent core made of loosely associated hydrophilic materials such as wood pulp. These prior art products are held in place by providing areas of pressure sensitive adhesive on the garment facing side to adhere it to the inner crotch surface of the wearer's undergarment.

One drawback of prior art absorbent articles has been that in the course of wearing the absorbent article, the shape of the absorbent article tends to deform and the article tends to move out of position, thereby reducing its effectiveness. Recent designs have addressed this problem by including tabs or wings that extend laterally from the longitudinal sides of the central absorbent and wrap around the edges of the undergarment. See U.S. Pat. No. 4,285,343 (McNair); U.S. Pat. No. 4,589,876 (Van Tilburg); and U.S. Pat. No. 4,911,701 (Mavinkurve). However, the use of such tabbed articles presents several problems.

First, such tabbed absorbent articles were previously made with integral tabs by (i) cutting a tabbed article shape from an extra-wide strip of laminate formed from layers of body fluid pervious and impervious materials and (ii) inserting a central absorbent core between the layers. However, this method has several disadvantages. First, there is considerable wastage due to the excess material remaining after the tabbed article shape is cut from the large strip. Second, the tab material is limited to that suitable for an absorbent article cover.

Recently, absorbent articles have been developed which have separately formed tabs which are attached to the garment facing side of the napkin—see U.S. Pat. No. 4,900,320 (McCoy). Consequently, it would be desirable to develop a method and apparatus for forming such separate tabs and attaching them to absorbent articles which (i) made efficient use of tab material, (ii) allowed the tabs to be made from a range of materials beyond those suitable for article covers and (iii) provided flexibility in terms of the location and orientation of the tabs on the article.

The second problem associated with the use of tabbed articles arises because adhesive strips are typically applied to both the tabs and the central portion for attaching the article to the user's undergarment. These adhesive strips are often covered with separate protective release strips which act to protect the adhesive from dirt and unintended adhesion during manufacture, packaging and storage. These release strips must be removed by the user just prior to application of the product. Multiple adhesive elements and release strips, however, can present the user with a cumbersome process when preparing the product for use. The user often has to remove all three release strips (one on the central absorbent core and one on each of the tabs) while simultaneously making sure that the tabs do not inadvertently adhere to one another or to another part of the product. In particular, the user must carefully handle the product when removing the release strip on one tab in order to avoid inadvertently contacting the exposed adhesive on the other tab and the central portion, thereby rendering the product useless. Even when the problem of undesired adhesion is avoided, the user is presented with the task of disposing of three release strips.

Accordingly, absorbent articles have been developed in which a single release strip, coated on both sides with silicone or the like, is used to protect the adhesive strips on both the central portion and tabs, so that a single pull of a release strip is sufficient to ready the article for use—see U.S. Pat. No. 4,701,178 (Glaug et al.). However, such double sided release strips are more expensive than the standard single sided release strips and present problems in manufacture because they are difficult to handle due to the slipperiness of both of their sides. Thus, a need exists for a tabbed absorbent article having a user-convenient arrangement in which a single pull of a release strip is sufficient to remove the release material covering both the central portion and tab adhesive strips yet which utilizes standard single sided release paper.

A third problem is that even though the tabs help to stabilize the article, as a result of forces imposed on it during use, the article may still shift and deform, causing a phenomenon known as "roping," whereby the napkin is crushed transversely inward and its edges are curled around its longitudinal axis so that the napkin eventually takes on the appearance of a twisted rope. This situation causes discomfort to the user and a loss of product effectiveness. Although it is known to attach the tabs along the longitudinal edges of the central portion of an absorbent article—see U.S. Pat. No. 4,285,343 (McNair)—there is a need for an absorbent article having tabs which are attached to the longitudinal sides of the central portion in such a way as to aid the article in resisting such lateral deformation.

SUMMARY OF THE INVENTION

It is an object of the current invention to provide a method and apparatus for efficiently making absorbent articles having attached tabs.

It is another object of the invention to provide a method of making and attaching the tabs which allows flexibility in the selection of tab material and in the placement and orientation of the tabs on the absorbent article.

It is still another object of the invention to provide an absorbent article having adhesive strips on both the central portion and the tabs which are protected by single sided release strips and yet which can be readied for application to an undergarment by a single pull on one release strip.

It is yet another object of the invention to provide an absorbent article having tabs which are attached in such a way as to aid the absorbent article in resisting lateral deformation.

These and other objects are accomplished using a method and apparatus whereby a pressure sensitive adhesive covered by a release strip is affixed to a strip of tab material. A continuous cut is made in the strip of tab material so that the cut alternates from side to side transversely across the centerline of the strip. The cut is made using a rotary die having a knife blade circumferentially extending around a drum in an approximately sinusoidal shape. As a result of this cut, the strip of tab material is transformed into two nested strips of tabs. The tabs in each strip face inward and are aligned in an offset fashion. In one embodiment of the invention, each of the strips is rotated approximately 180° so that the tabs face outward. The tabs are then spaced apart and realigned so that the tabs from each strip are in an in-line alignment. The realignment is done by separating the strips, conveying one strip a predetermined distance greater than the other strip and then bringing the tab strips together again. In one embodiment, realignment is accomplished by passing each tab strip around separate drums, the drums being spaced apart a predetermined distance equal to one half the tab pitch. The tab strips are then cut into tab pairs. The tab pairs are transported by a vacuum drum and deposited onto a strip of absorbent article to which an adhesive has been applied. The tabs are then folded over the strip and the strip is cut into individual absorbent articles. In an alternate embodiment the tab pairs are attached to a first layer of material which is then attached to a second layer of material on which an absorbent core is disposed, thereby enclosing the absorbent core.

An absorbent article made by the aforementioned method and apparatus is also provided. The article has a central portion and tabs attached to longitudinally extending sides of the central portion. The central portion has an article release strip covering pressure sensitive adhesive strips on its garment facing side and the tabs have tab release strips covering pressure sensitive adhesive strips on their garment facing sides. The tabs are disposed over the garment facing side of the central portion and adhesive is applied between the article release strip and tab release strips, attaching each to the other so that both the article release strip and the tab release strips can be removed by a single pull on the article release strip. The tabs may be attached to the portions of the longitudinally extending sides of the central portion which are adjacent the body facing side of the article. This arrangement preferentially creates tension in the pervious cover forming the body facing side, thereby creating compressiive forces acting on the absorbent core which aid it in resisting lateral deformation.

BRIEF DESCRIPTION OF THE DRAWINGS

FIG. 3 is a transverse cross-section through two embodiments of an absorbent article produced according to the method of the current invention.

DESCRIPTION OF THE PREFERRED EMBODIMENT

Figure 1:
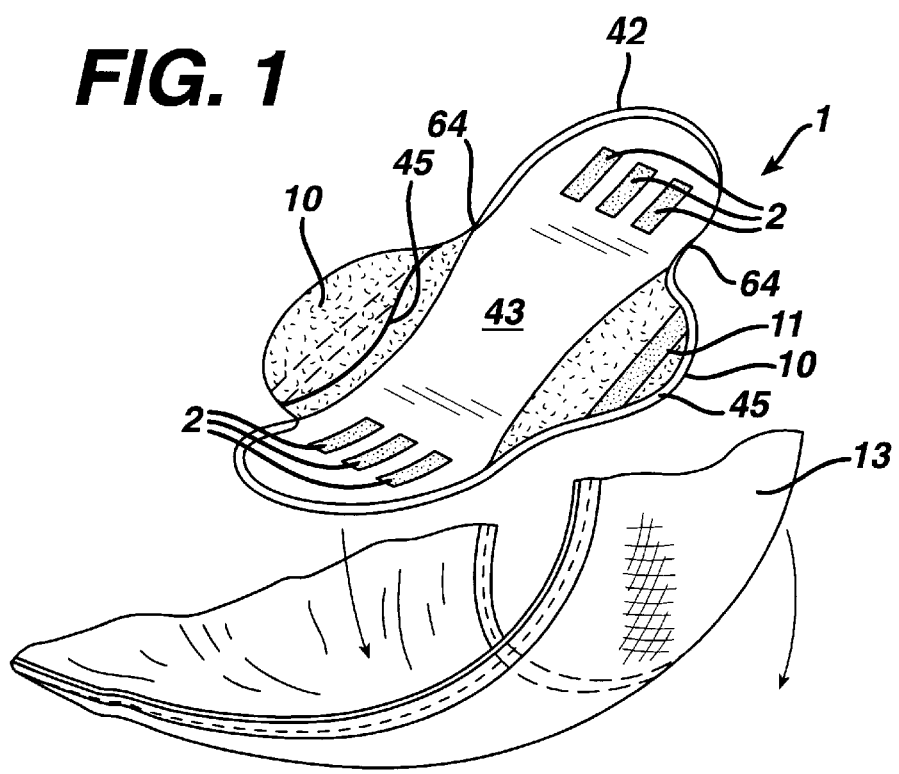
FIG. 1 is an isometric view of the absorbent article according to the current invention being applied to an undergarment.
Figure 2:
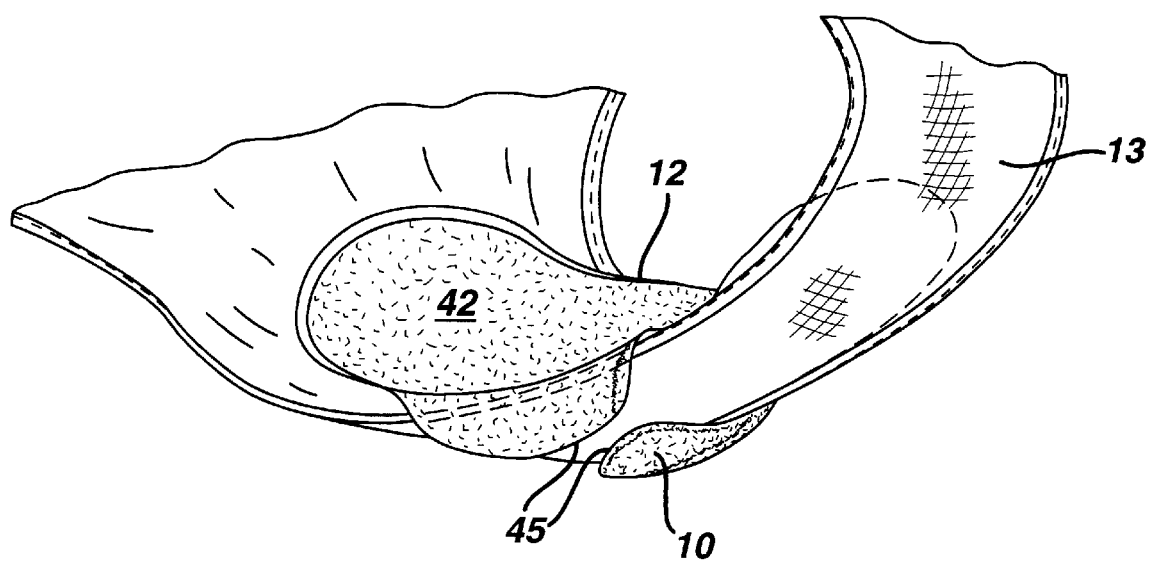
FIG. 2 is an isometric view of the absorbent article shown in FIG. 1 as applied to an undergarment.

There is shown in FIG. 1 a sanitary napkin 1 of the type made by the method of the current invention. The napkin is comprised of a longitudinally extending central portion 12 having longitudinal sides 64 and transverse edges. Tabs or wing segments 10 are attached at each of the longitudinal sides 64. The napkin 1 is applied to the crotch 13 of a panty by placing the garment facing side 43 of the napkin against the inside surface of the crotch. Adhesive strips 2 on the garment facing side 43 help maintain the napkin in place. In addition, the tabs 10 are folded around the crotch 13 so that the edges 45 of the tabs nearly abut each other, as shown in FIG. 2. The tabs serve to further stabilize the napkin and prevent side leakage. Adhesive strips 11 on the tabs 10 secure the tabs to the crotch 13.

The construction the tabbed napkin 1 shown in FIG. 1 is shown in FIG. 3(a). In the central portion 12 of the napkin is an absorbent core 5. As is known in the art, the absorbent core 5 may be comprised of a loosely associated absorbent hydrophilic material such as cellulose fibers, wood pulp, regenerated cellulose or cotton fibers, or other absorbent materials generally known in the art, including peat moss or super-absorbent materials.

The side 42 of the napkin, which is intended to be worn against the body of the user, is covered by a body-fluid pervious cover 6 which can be any resilient, relatively non-absorbing fluid pervious material. This material is provided for comfort and directs fluid to the underlying core 5, which retains the fluid. The cover should retain little or no fluid in its structure to provide a relatively dry surface next to the skin. The fluid pervious cover 6 is preferably a non-woven fabric made of fibers or filaments of thermoplastic polymers such as polyethylene or polypropylene, or an apertured polymeric film. Generally, the fluid pervious cover 6 is a single, rectangular sheet of material having a width sufficient to cover the body-facing side of the napkin. As shown in FIG. 3(a), the fluid pervious cover 6 may extend around the sides of the core 5 in a C-shaped configuration. Preferably, the fluid pervious cover 6 is longer than the core 5 so as to form end transverse ends, which may be sealed with other pervious or non-pervious layers to fully enclose the core.

The napkin 1 further comprises a body fluid impervious barrier 7 on its garment facing side 43. The impervious barrier 7 may be heat sealed or, as shown in FIG. 3(a), attached to the pervious cover 6 by an adhesive 8. The impervious barrier 7 may comprise any thin, flexible, body fluid impermeable material such as a polymeric film—for example, polyethylene, polypropylene, cellophane or even a normally fluid pervious material that has been treated to be impervious, such as impregnated fluid repellent paper or non-woven fabric material.

Alternatively, the central portion 12 of the napkin could be formed from an absorbent core 5 having integral body facing 42 and garment facing 43 sides—that is, without separate layers of a body fluid pervious cover 6 and a body fluid impervious barrier 7.

Figure 6:
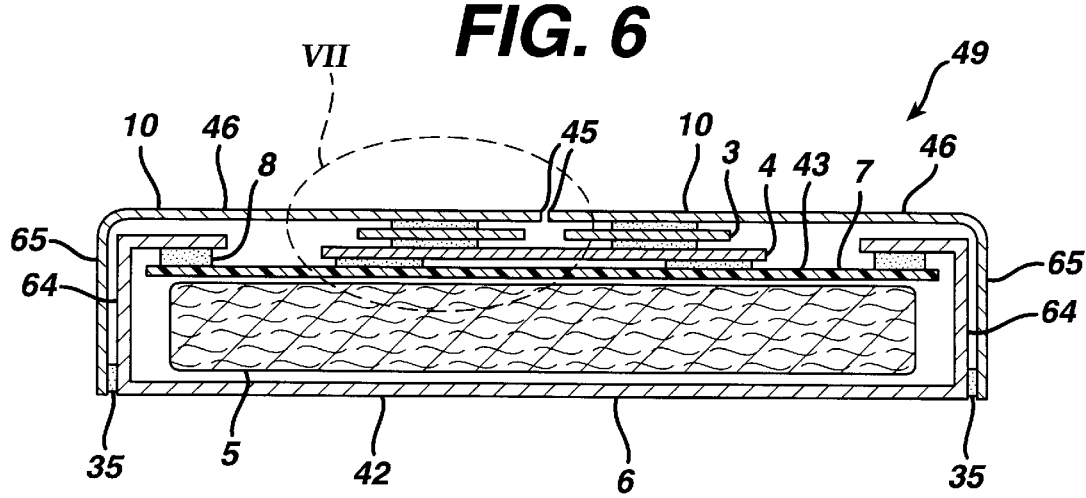
FIG. 6 is a cross-section taken through line VI—VI shown in FIG. 5.

Tabs 10 extend laterally from the napkin central portion 12. As shown in FIG. 3(a), the base portion 65 of each tab 10 is attached to the edges of the impervious barrier 7. Alternatively, the tabs could be attached between the longitudinal edges of the pervious cover 6 and the impervious barrier 7, as shown for the napkin 47 shown in FIG. 3(b), or attached to the longitudinal sides 64 of the napkin, as shown in FIG. 6. As discussed further below, attaching the tabs 10 to the longitudinal sides 64 of a napkin as shown in FIG. 6 yields important advantages. Note that, as shown in FIG. 6, the tabs 10 can be folded over the central portion 12 to facilitate storage and packaging. To apply the napkin 1 to an undergarment, the tabs are extended as shown in FIG. 3(a).

Although preferably not including absorbent pulp materials, the tabs 10 can include a body fluid impervious backing such as the materials described in connection with the above-mentioned body fluid impervious barrier 7. It is also expected that the tabs 10 can comprise a body fluid pervious material, much like the above-mentioned body fluid pervious cover 6. In the preferred embodiment, the tabs 10 contain absorbent tissue with sufficient capillary action to retain small quantities of escaped liquid. This tissue can be heat sealed or adhesively sealed around the edges of the tabs 10 to form absorbent areas. However, according to an important aspect of the current invention, the tab material need not be of the type suitable for a pervious cover 6 or an impervious barrier 7, since the tabs 10 are formed separately, as discussed further below.

As shown in FIG. 3(a), pressure sensitive adhesive strips 2 and 11 are applied to the garment facing side 43 of the napkin and the tabs 10, respectively. As used herein, the term "pressure-sensitive" refers to any releasable adhesive or releasable tenacious means. Adhesive compositions suitable for sanitary napkins, include, for example, water-based pressure-sensitive adhesives such as acrylate adhesives. Alternatively, the adhesive may comprise rapid setting thermoplastic "hot melt", rubber adhesives or two-sided adhesive tape.

As is customary in the art, paper release strips 3 and 4, which have been coated on one side, can be applied to protect the adhesive strips 2 and 11 prior to use. The coating, which may be silicone, reduces the adherency of the coated side of the release strip to the adhesive as compared to uncoated side of the release strip. The release strip can be formed from any suitable sheet-like material which, when coated, adheres with sufficient tenacity to the adhesive to remain in place prior to use but which can be readily removed when the napkin is to be used.

Figure 4:
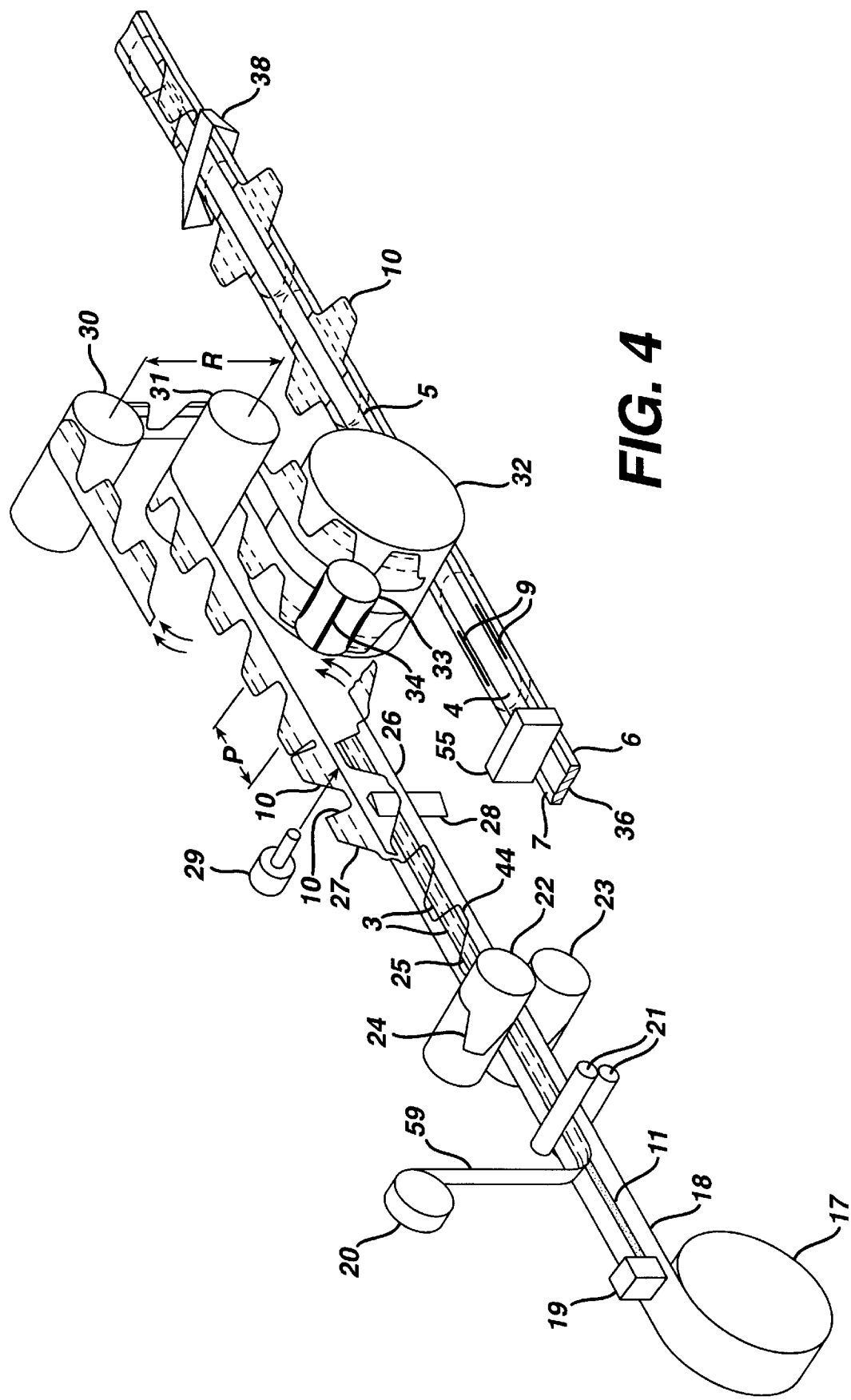
FIG. 4 is an isometric view, partially schematic, of a production line according to the current invention for producing the absorbent article shown in FIG. 3(a).

A production line for making the napkin 1 is shown in FIG. 4. A strip 18 of the aforementioned tab 10 material is unwound from a roll 17 and passed under an adhesive gun 19. The adhesive gun 19 applies a continuous strip of pressure sensitive adhesive 11, as described above, along the centerline of the strip of tab material. A strip of release paper 59 is unwound from a role 20 and its coated side is applied over the adhesive strip 11. A pair of nip rollers 21 press the release strip 59 onto the tab material strip 18.

After application of the release strip 59, the tab material strip 18 passes between upper 22 and lower 23 drums. A knife blade 24 extends around the circumference of the upper drum 22 so that the upper drum forms a rotary die. The lower drum 23 has a hardened surface which acts as an anvil for the rotary die 22. As the knife blade 24 extends circumferentially around the drum 22 it alternates back and forth around the transverse centerline of the drum so that, if laid flat, the knife blade would be formed in the shape desired for the edges of the tabs 10. As shown in FIG. 4, the rotary die 22 makes a continuous approximately sinusoidal longitudinal cut 25 which alternates symmetrically from side to side transversely across the centerline of the tab material strip 18, the cut alternating between being closer to one longitudinal edge and then the other longitudinal edge of the tab material strip 18. As a result, the tab material strip 18 is cut into two tab strips 26, 27. Each tab strip 26, 27 is comprised of a plurality of adjacent tabs 10 arranged in a row.

Figure 12:
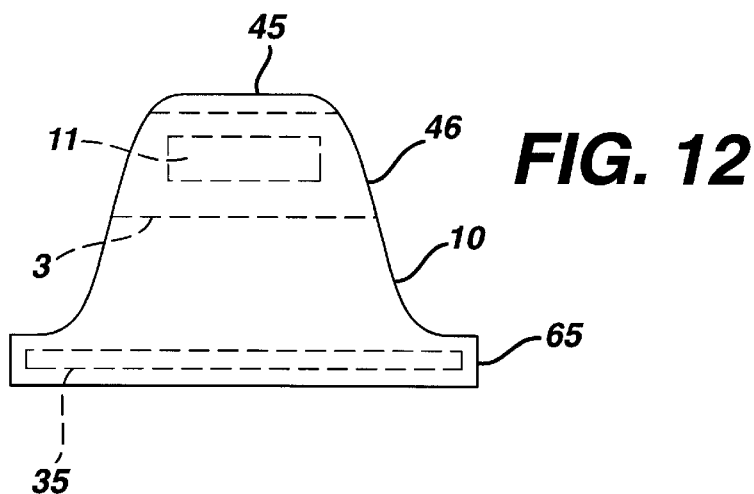
FIG. 12 shows a tab according to the current invention.
Figure 15:
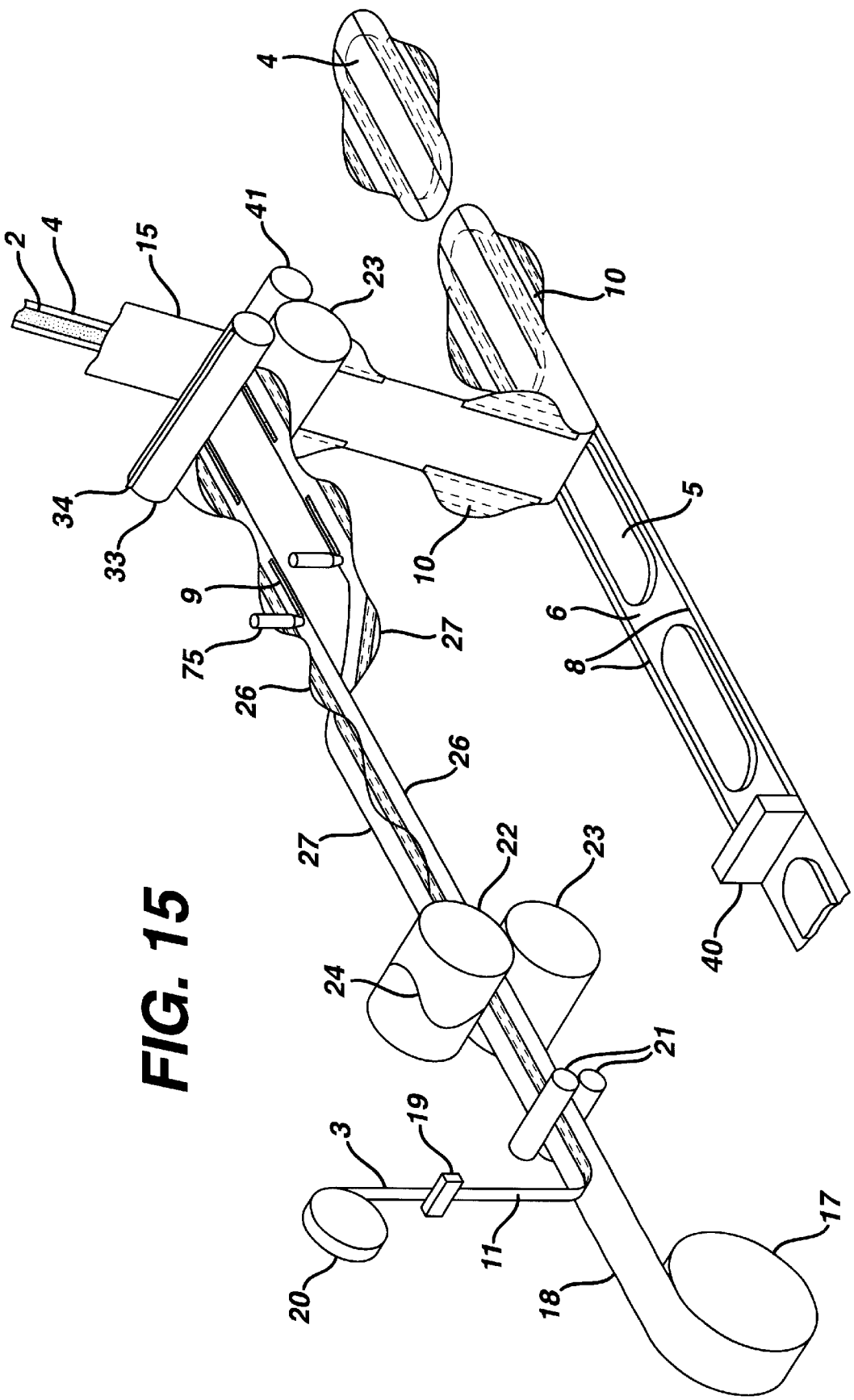
FIG. 15 is an isometric view, partially schematic, of an alternate embodiment of the production line shown in FIG. 4.

As shown in FIGS. 4 and 12, each tab 10 has an approximately trapezoidal shaped tip portion 46 and an elongated rectangular base portion 65. The short edge of the trapezoid forms the tab edge 45 and the long edge of the trapezoid is contiguous with the elongated rectangular base portion 65. Thus, the tab strips 26, 27 have an approximately truncated saw-tooth shape. Alternatively, as shown in FIG. 15, the edges of the tab strips 26, 27 can be given a completely sinusoidal shape. As previously discussed, the base 65 of each tab 10 serves as the point of attachment between the tabs and the napkin 1. Although the tab shapes shown in FIGS. 12 and 15 are thought to be preferred by users, those skilled in the art will appreciate that, according to the method taught by the current invention, tabs can be formed from a large variety of shapes.

As shown in FIG. 4, each tab is contiguous with the adjacent tabs at its base 65 so as to form a long strip of tabs arranged in a row. The tabs 10 in each tab strip 26, 27 are inward facing—that is, the tab bases 65 lie along the external longitudinal edges of the tab strip and the tips of the tabs in each strip extend toward the other tab strip in a nested arrangement. As a result of the cutting action of blade 24, the release strip 59 has been cut so that a section 3 of release strip is attached to each tab 10.

As shown in FIG. 4, a stationary plow 28 is disposed between the tab strips 26, 27—that is, at the centerline of the path of the tab material strip 18. The plow 28 separates the tab strips 26, 27 and causes them to rotate approximately 90° in opposite directions into the vertical orientation. The tab strips 26, 27 are then conveyed past two air nozzles 29 (only one of which is shown) which direct jets of air onto the tab strips causing them to rotate another 90° in opposite directions into the horizontal orientation. Thus, the combined effect of the plow 28 and nozzles 29 is to reverse the orientation of the tab strips 26, 27 from inward to outward facing, so that the cut edges formed in each tab strip by the rotary die 22 which initially faced toward each other are made to face away from each other.

As shown in FIG. 4, the aforementioned shape of the cut 25 causes the tabs 10 in each of the tab strips to be in an offset alignment in the longitudinal direction with respect to the tabs in the other tab strip—that is, the tabs strips are out of phase so the each tab 10 is interposed between adjacent tabs in the other tab strip in a nested arrangement. Since it is desired to have two tabs, one tab from each of the tab strips, applied to each napkin in a longitudinally aligned fashion, the tab strips are realigned so as to be in an in-line alignment—that is, aligned in-phase so that the tabs in each strip are in the same longitudinal position.

This realignment is accomplished by passing tab strip 26 over an upper cylindrical member 30 and tab strip 27 over a lower cylindrical member 31. The cylindrical members 30 and 31, which may be drums or rods, are spaced apart in a direction perpendicular to the initial plane of the tab strips by a distance R which is equal to one half the pitch P between the tabs 10 in each tab strip. Thus, the tabs 10 in tab strip 26 travel further than those in tab strip 27 by one half the distance P so that when the tab strips are once again brought together into the same horizontal plane, the tabs 10 in each strip are aligned side by side, as shown in FIG. 4.

Following alignment, the tab strips are passed between a vacuum drum 32 and a cutting drum 33. The cutting drum 33 has a plurality of longitudinally extending knife blades 34 (referred to as a "flying knives" or "flex knives") spaced around the circumference of the drum by a distance equal to the tab pitch P. The knife blades 34 are spaced and indexed with respect to the vacuum drum so that intermittent hardened surfaces formed therein act as anvils for the knife blades. Drum 33 is operated in timed relationship with the movement of the tab strips 26, 27 so that it cuts the tab strips into pairs of tabs 10. The tab pairs are held on the vacuum drum 32 by the suction created therein. Note that a portion of the release strip 3 and adhesive 11 remains on the tip of each tab after the step of cutting the tab strips into tab pairs is performed.

A sanitary napkin strip 36 is passed under the vacuum drum 32. As shown in FIG. 4, the napkin strip 36 is comprised of a plurality of pre-cut absorbent cores 5 enclosed by strips of a body fluid impervious barrier 7 and a body fluid pervious cover 6, as previously discussed and as shown in FIG. 3(a). An adhesive nozzle 55 intermittently deposits two aligned strips of adhesive 9 along the edges of the napkin strip 36—more specifically, along the edges of the impervious barrier 7. The vacuum drum 32 is then pressed into the napkin strip 36 so as to plow the bases 65 of the tabs 10 into the napkin along the adhesive strips 9. This plowing action, along with the tack of the adhesive 9 and the timed release of the vacuum in the vacuum drum 32, causes the tabs 10 to be deposited and attached onto the napkin strip at the tab bases 65. Note that the central portion release strip 4 could be applied to the garment facing side 43 of the napkin strip either before or after the tabs 10 are attached.

After the tabs 10 are attached, the napkin strip 36 then passes through a folder 38, shown in FIG. 4 as a sheet metal box having inwardly tapering sides. The folder 38 folds the tabs over the central portion 12 into the orientation shown in FIG. 6 to facilitate storage and packaging. Finally, the napkin strip is cut (not shown) into individual napkins—for example by a flying or flex knife, such as that previously discussed—and the transverse ends of the impervious barrier 7 and pervious cover 6 are sealed by heat or adhesive means.

Many modifications are possible with respect to the method and apparatus for forming and attaching the tabs shown in FIG. 4. For example, the tab strips 26, 27 could be rotated using either plows or air nozzles exclusively. The glue nozzle 55 could be arranged to apply adhesive 9 to the tabs 10 rather than the napkin strip 36. The napkin strip 36 could be flipped over so that the tabs 10 were applied to the body facing side 43. The absorbent core 5 in the napkin strip 36 could be a continuous length of material rather than the pre-cut portions shown in FIG. 4 or the absorbent core 5 could feature integral body facing and garment facing sides to which the tabs 10 are directly attached. Also, individual napkins 1 could be directed under the vacuum drum 32 rather than the continuous napkin strip 36.

Figure 10:
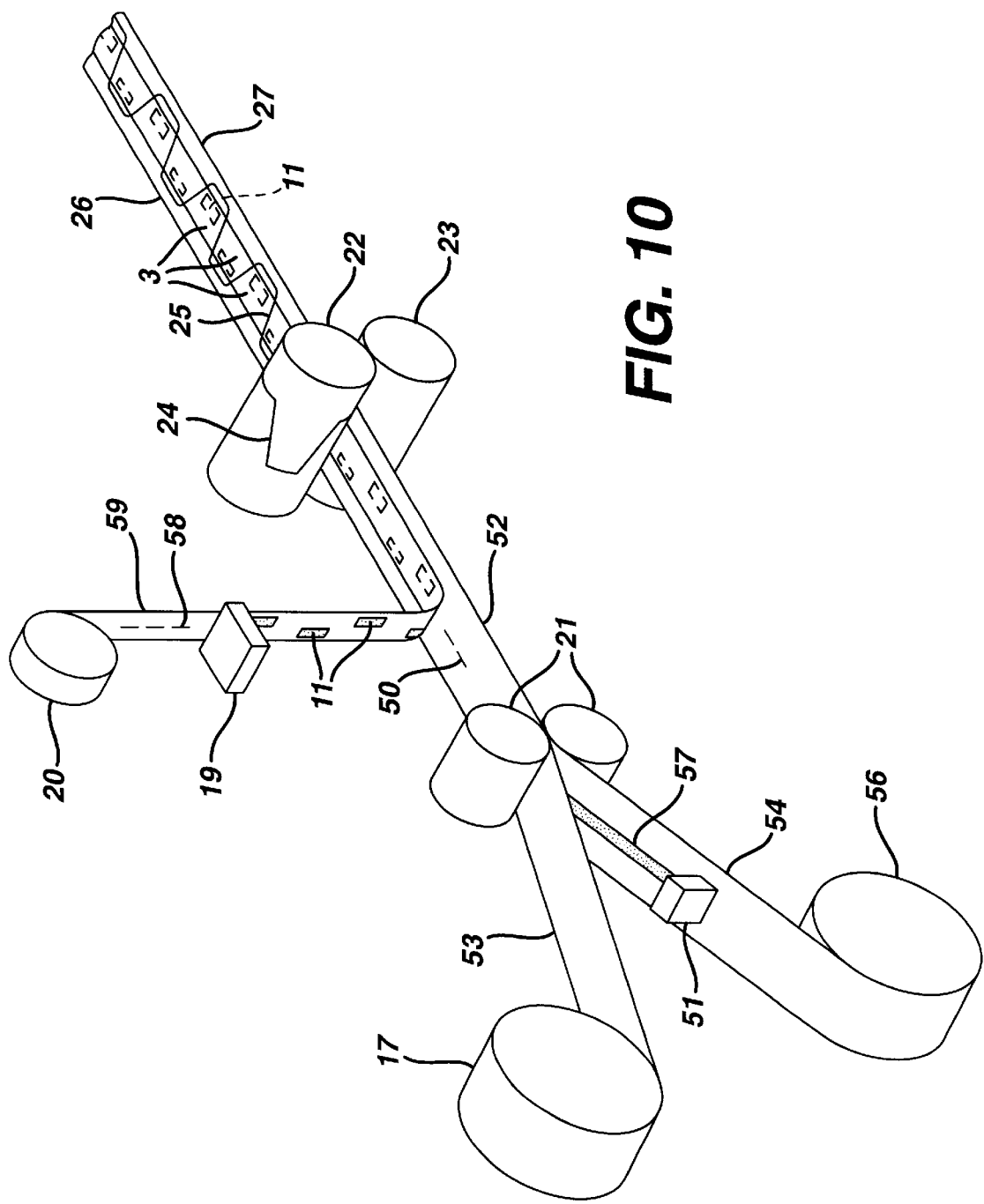
FIG. 10 is an isometric view, partially schematic, of an alternate embodiment of the first portion of the production line shown on FIG. 4.

FIG. 10 shows an alternate embodiment of the first portion of the production line shown in FIG. 4. As shown in FIG. 10, the tabs 10 are cut from a laminate of two strips of tab material 53 and 54 unwound from rolls 17 and 56, respectively, and formed into a strip of tab material laminate 52. The strips of tab material 53 and 54 can be made from any of the materials previously discussed as being suitable for use as the body fluid pervious cover 6 or the body fluid impervious barrier 7. Alternatively, the strips 53 and 54 can be formed from other materials not suitable as a pervious cover or impervious barrier. The layers 53, 54 are bonded together with adhesive 57 applied by nozzle 51. This bonding is facilitated by nip rollers 21 which press the layers 53, 54 together.

As also shown in FIG. 10, the adhesive 11 can be initially applied to the release strip 59 directly, rather than to the tab strip material as shown in FIG. 4. Moreover, in the embodiment shown in FIG. 10, the adhesive is applied to the release strip 59 in intermittent strips 11 which alternate on either side of the centerline 58 of the release strip in a staggered arrangement so that one strip of adhesive is disposed on each tab in the center top portion of the tip 46, as shown in FIG. 12. As a result, the knife blade 24 does not cut through the adhesive strip 11, thereby avoiding cleanup due to adhesive contamination. After the adhesive is applied, the release strip 59 is then attached to the tab laminate strip 52, the adhesive strips 11 being disposed between the release strip 59 and the tab material laminate 52. A pair of nip rollers (not shown) may be used to press the release strip 50 onto the tab laminate strip 18.

Figure 5:
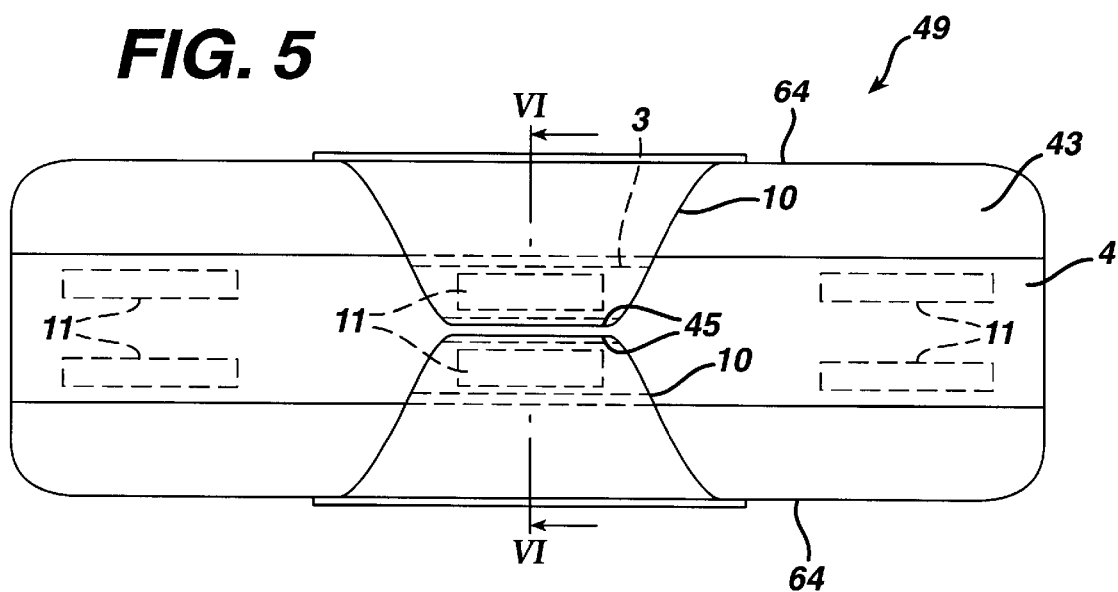
FIG. 5 is a plan view of the garment facing side of an absorbent article according to the current invention ready for packaging.
Figure 7:
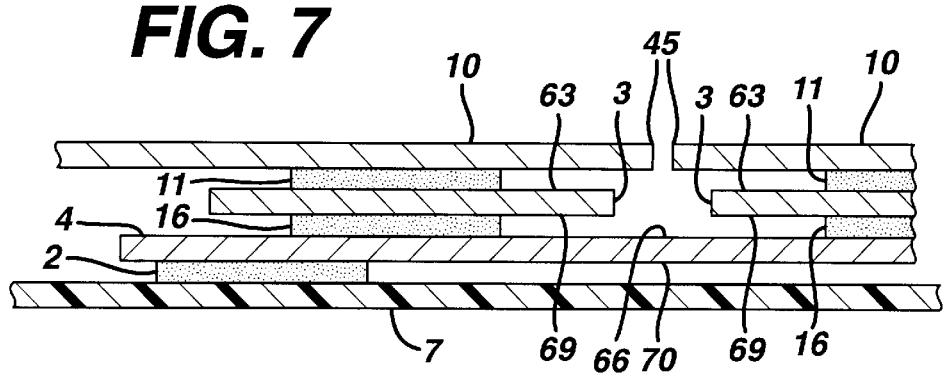
FIG. 7 is an enlarged view of the portion of FIG. 6 enclosed by the ellipse marked VII.

FIGS. 5–7 show one particularly desirable alternate embodiment of the napkins shown in FIG. 3. As shown in FIG. 6, the tabs 10 of the napkin 49 are in their folded configuration to facilitate storage and packaging. In the folded configuration, the tips 45 of each tab 10 are disposed adjacent to each other along the longitudinal centerline of the napkin. To apply the napkin 49 to an undergarment, the tabs are extended, as shown in FIG. 1, and then folded around the panty crotch 13 so that the edges 45 of the tab tips abut one another, as shown in FIG. 2.

Figure 8:
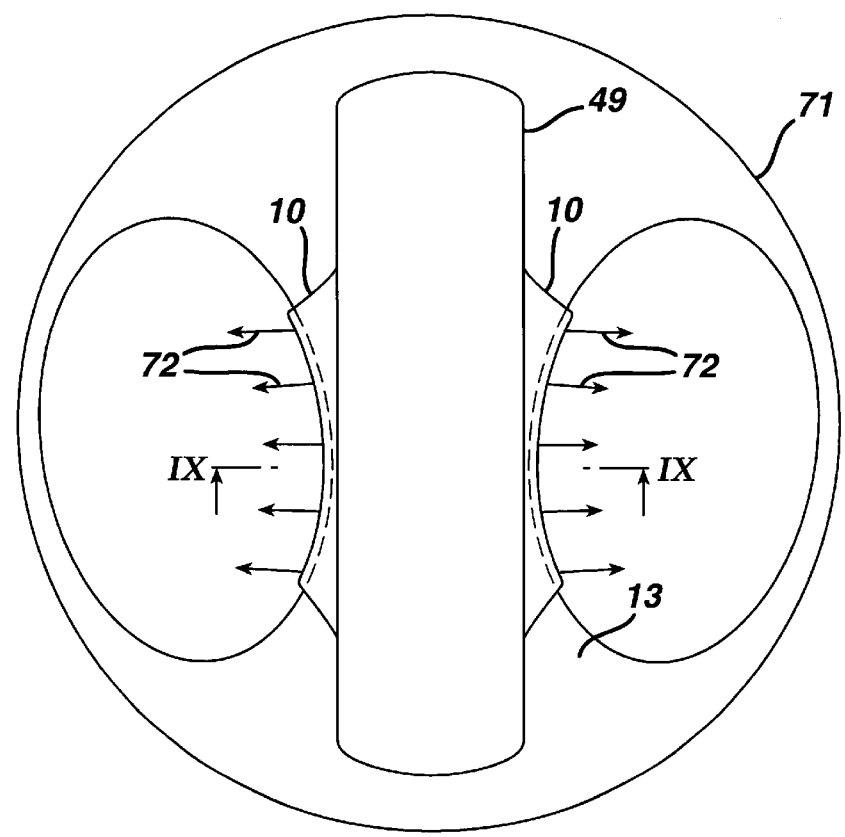
FIG. 8 is a plan view of a napkin according to the current invention as applied to the crotch of a panty.
Figure 9:
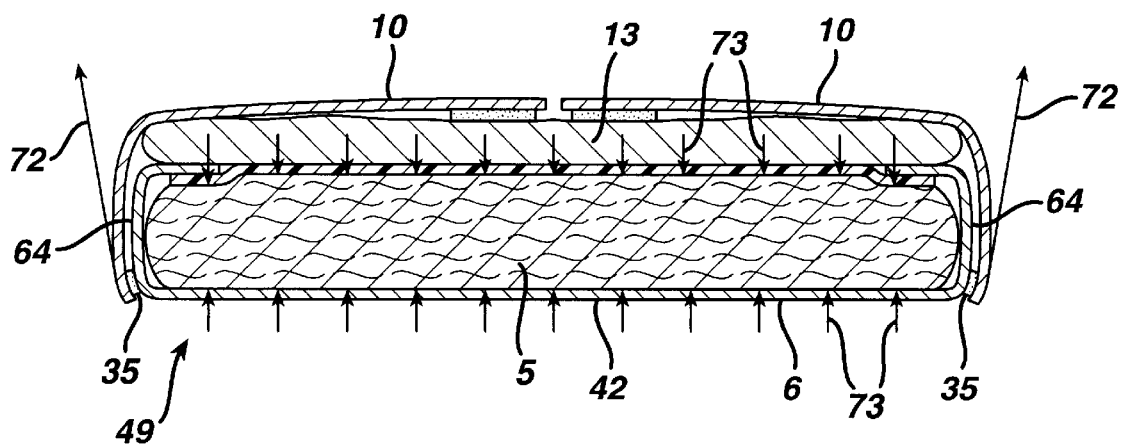
FIG. 9 is a cross-section taken through line IX—IX shown in FIG. 8.

As shown in FIG. 6, the edges of the pervious cover 6 form the longitudinal sides 64 of the central portion of the napkin 49. According to an important aspect of the current invention, the base 65 of each tab 10 is attached to the portion of the longitudinal sides 64 immediately adjacent the body facing side 42 by adhesive 35. As shown in FIG. 8, wrapping the tabs 10 around the crotch 13 of a panty 71 causes the panty crotch to exert forces 72 on the napkin 49 As shown in FIG. 9, these tensile forces 72 are transmitted through the tabs 10 to the pervious cover 6 on the body facing side 42, thereby placing it in tension. As a result of the pervious cover 6 being pulled in opposite transverse directions by the tensile forces 72, the absorbent core 5 is pulled against the panty crotch 13 so that compressive forces 73 are imparted to the core. These compressive forces 73 have the important effect of preventing the absorbent core 5 from collapsing in the transverse direction during use. Thus, attaching the tab bases 65 to the portions of the longitudinally extending sides 64 which are adjacent the body facing side 42 so as to preferentially create tension forces in the body facing side, rather than in the garment facing side 43, offers a unique advantage not found in prior art napkins in which the tabs are attached to the edges of both the body and garment facing sides.

As shown in FIG. 7, the coated side 70 of the paper release strip 4 is applied against the napkin adhesive strips 2 to protect them prior to use. As is typical, only side 70 of the release strip 4 is coated. As also shown in FIG. 7, the coated side 63 of the release strip 3 is applied against the adhesive strip 11 on each tab tip 46. As in the case of the napkin release strip 4, only sides 63 of the tab release strips 3 are coated. In the embodiment shown in FIGS. 5–7, adhesive strips 16 attach uncoated side 69 of each of the tab release strips 3 to uncoated side 66 of the napkin release strip 4. Thus, the coated sides 63 and 70 of release strips 3 and 4, respectively, are applied to adhesive strips 2 and 11, respectively, whereas uncoated sides 69 and 66 are attached to each other by adhesive strip 16.

As a result of this release strip arrangement, pulling on the napkin release strip 4 will cause it and both of the tab release strips 3 to be removed from the napkin as a unit, thereby exposing both the napkin adhesive strips 2 and tab adhesive strips 11. Thus, the user can ready the article for application to the undergarment by a single pull of the napkin release strip 4. Moreover, this single-release-strip-pull feature is achieved without the aforementioned expense and disadvantages associated with using a release strip coated on both of its sides as taught by the prior art.

Figure 11:
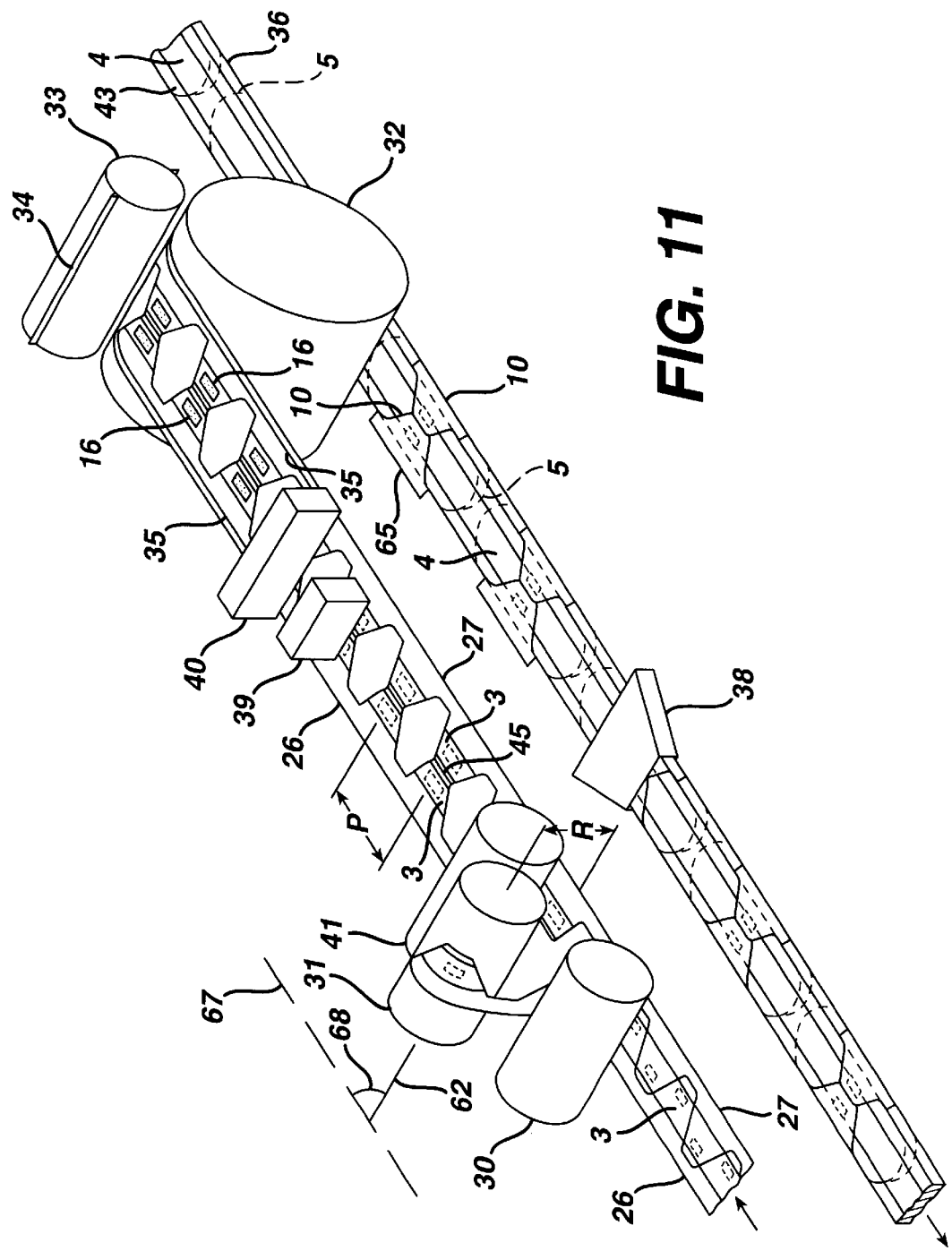
FIG. 11 is an isometric view, partially schematic, of an alternate embodiment of the second portion of the production line shown in FIG. 4.

FIG. 11 shows an alternate embodiment of the second portion of the production line shown in FIG. 4 which is adapted to produce the napkin 49 shown in FIGS. 5–7. In this embodiment, the tab strips 26, 27 are formed as before and are realigned to the aforementioned in-line alignment using cylindrical members 30, 31 and 41 by causing tab strip 26 to travel further than tab strip 27 by one half the tab pitch.

However, in this embodiment, in addition to longitudinal realignment, cylindrical members 30, 31 and 41 also offsets tab strip 26 transversely. The amount of the offset is approximately equal to the height of the tip portion 46 of the tabs—that is, the distance between the long and short edges of the trapezoid—so that, instead of the previous nested arrangement, the edges 45 of the tab tips abut one another, as shown in FIG. 11. This offsetting is accomplished by orienting the centerline 62 of cylindrical member 31 at an angle 68 of less than 90° to the direction 67 of the tab strip travel. Such realignment can be accomplished using a commercially available web tracking unit, such as Edge Guide Tracking Unit H6230-191-06 manufactured by North American Manufacturing Co., Clevand, Ohio.

Figure 13:
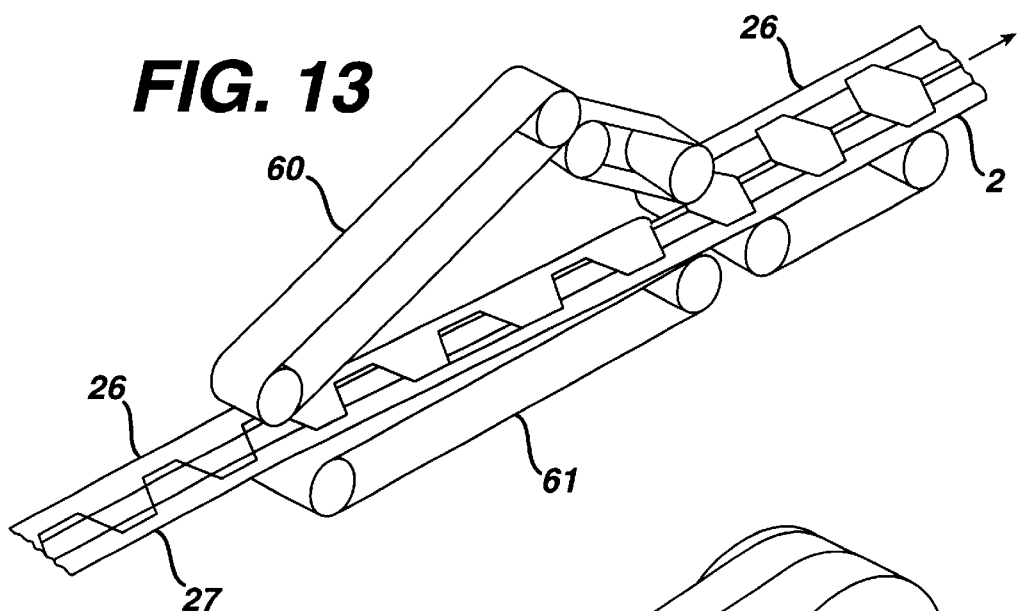
FIG. 13 shows an alternate embodiment of the portion of the production line shown in FIG. 11 which longitudinally realigns and transversely offsets the tab strips.

Alternatively, the tabs could be longitudinally aligned and transversely offset using vacuum conveyers 60 and 61, as shown in FIG. 13. The vacuum conveyors 60, 61 are aligned in the transverse direction so as to spread the tabs strips 26, 27 apart by the height of the tab tips and spaced in the direction perpendicular to the path of the tab strips so as to cause strip 26 to travel farther than strip 27 by an amount equal to one half the pitch between tabs.

Regardless of the method of realignment, adhesive nozzle 39 next applies two transversely spaced strips of intermittently applied adhesive 16, as shown in FIG. 11. The operation of nozzle 39 is timed with respect to the passage of the tab strips 26, 27 so that the adhesive strips 16 are spaced so that one adhesive strip is applied to the release strip section 3 on each tab tip 46. Immediately thereafter, adhesive nozzle 40 applies a second pair of transversely spaced strips of continuously applied adhesive 35 adjacent the outside edges of the tab strips 26, 27—that is, along the edge of the tab bases 65, as shown in FIG. 6. Alternatively, the adhesive 35 could be applied in intermittent strips, in which case the operation of nozzle 40 is timed with respect to the passage of the tab strips 26, 27 so that the adhesive strips 35 are spaced so that one adhesive strip is applied to the base 65 of each tab, with the adhesive strips 16 being longitudinally aligned with adhesive strips 35.

After application of the adhesive strips 16 and 35, the tab strips are cut into pairs of tabs 10 and applied to a napkin strip 36 as before except that initially, only the tips 46 of the tabs 10, rather than the bases 65, are attached to the napkin strip 36. This is accomplished by applying the tab release strips 3 to the napkin release strip 4 by means of the adhesive strips 16.

As shown in FIG. 11, the tabs are transversely spaced and the vacuum drum 32 is transversely aligned with respect to the napkin strip 36 so that when the release strips sections 3 are attached to the release strip 4, the base 65 of each tab overhangs one of the longitudinal edges of the garment facing side 43 of the napkin strip. The napkin strip 36 is then passed through a folder 38, shown in FIG. 4 as a sheet metal box surrounding the napkin strip and having an approximately trapezoidal shape. The inward tapering sides of the folder 38 folds each tab base 65 over the longitudinal edges of the napkins and plows the bases into the longitudinally extending sides 64 of the napkins so as to attach them thereto with the aid of adhesive strips 35, as shown in FIG. 6.

Figure 14:
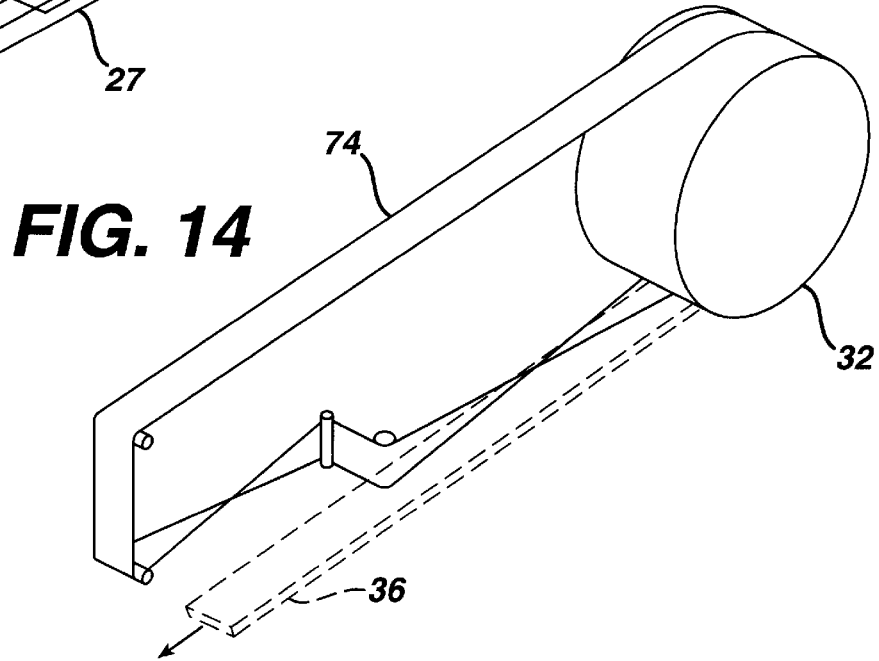
FIG. 14 shows as alternate embodiment of the portion of the production line shown in FIG. 11 which attaches the wing segments to the napkin strip.

Alternatively, the tab bases 65 could be plowed into the sides 64 by carring the tab pairs on two vacuum belts 74, one of which is shown in FIG. 14, rather than the using the folder 38 shown in FIG. 11. Each vacuum belt 74 presses the tip 46 of one of the tabs from each tab pair into the napkin strip 36 as before. However, the vacuum on the base 65 of the tab is not released upon contact with the napkin strip and, as shown in FIG. 14, the belt 74 is twisted so as to bend the base over into the vertical orientation and plow it into the side of the napkin. The vacuum on the belt 74 is then released so as to allow the base 65 to become attached to the side 64 by the adhesive strip 35.

FIG. 15 shows another alternate embodiment of the production line shown in FIG. 4 which is adapted to produce the napkin 47, shown in FIG. 3(b). As shown in FIG. 15, the tab strips 26, 27 are realigned and the tabs 10 are inverted from an inward facing to an outward facing orientation by crossing tab strip 27 under tab strip 26 and moving tab strip 27 transversely a predetermined distance, equal to one half the tab pitch as previously discussed. Unlike the embodiments shown in FIGS. 4 and 11, the tab strips remain in essentially the same horizontal plane during the realignment process.

As also shown in FIG. 15, the tab pairs may be attached, via adhesive strips 9 applied by guns 75, to a strip 15 of the impervious barrier 7 before the barrier is attached to the napkin. The combined barrier strip 15 and tab 10 pairs are then attached to a strip of the pervious cover 6, on which absorbent cores 5 have been disposed, using adhesive 8 applied by gun 40, so that the barrier strip 15 partially encloses the absorbent core 5. Alternatively, the embodiment shown in FIG. 15 may be practiced by attaching the tab pairs to a strip of pervious cover 6 and then attaching the combined pervious cover strip and tab pairs to the impervious barrier 7.

As the foregoing indicates, the method of the current invention affords great flexibility in the design of sanitary napkins having attached tabs, allowing the use of a wide range of tab materials and allowing the tabs to be attached to the napkin in various ways to achieve an optimum configuration. As the various embodiments disclosed above indicate, the present invention may be embodied in many specific forms without departing from the spirit or essential attributes thereof and, accordingly, reference should be made to the appended claims, rather than to the foregoing specification, as indicating the scope of the invention.

What is claimed is:

1. A method of making an absorbent article having longitudinal sides and tabs which extend laterally from a central portion of the longitudinal sides of the absorbent article, wherein said tabs are adapted to be folded around the crotch of a user's undergarment, comprising the steps of:

a) making a continuous longitudinal cut in a strip of tab material having a longitudinal center line, said cut alternating from side to side transversely across said longitudinal center line of said strip of tab material, whereby said strip is cut into first and second tab strips having inward extending nested tabs in a longitudinally offset alignment;

b) realigning said first and second tab strips so that said tabs are in a longitudinally in-line alignment;

c) cutting said first and second tab strips into pairs of individual tabs; and d) bonding said tab pairs to the central portion of the longitudinal sides of said absorbent article.

2. The method according to claim 1 wherein the step of making said continuous longitudinal cut comprises the step of making an approximately sinusoidal cut symmetrically disposed about the centerline of said tab material strip.

3. The method according to claim 1 further comprising the step of inverting said first and second tab strips so that said tabs extend outward prior to the step of attaching said tab pairs to said absorbent article.

4. The method according to claim 3 wherein the step of inverting said tab strips comprises the step of rotating said tab strips approximately 180°.

5. The method according to claim 3 wherein the step of making said continous cut comprises the step of passing said tab material strip under a rotary die.

6. The method according to claim 1 wherein the step of realigning said tab strips comprises the steps of:

a) separating said first and second tab strips;

b) conveying said first tab strip a predetermined distance farther than said second tab strip; and c) bringing said first and second tab strips together.

7. The method according to claim 6 wherein said predetermined distance is equal to approximately one half the pitch between adjacent tabs on said tab strips.

8. The method according to claim 1 wherein the step of attaching said tab pairs to said absorbent article comprises the steps of:

a) conveying said tab pairs at least partially around a drum;

b) passing said absorbent article under said drum; and c) pressing said drum into said absorbent article.

9. The method according to claim 8 wherein the step of conveying said tab pairs around said drum comprises the step of maintaining said tab pairs on said drum by suction.

10. The method according to claim 1 wherein said absorbent article has longitudinally extending sides and the step of attaching said tab pairs to said absorbent article comprises the step of attaching said tab pairs to said longitudinally extending sides.

11. The method according to claim 1 further comprising the step of attaching a release strip to said strip of tab material prior to the step of making said continuous longitudinal cut.

12. The method according to claim 11 wherein the step of applying said release strip comprises the step of applying said release strip along the center line of said strip of tab material, whereby a portion of said release strip remains on each of said tabs after the step of cutting said tab strips into tab pairs.

* * * * *